United States Patent
Wang et al.

(10) Patent No.: US 12,280,138 B2
(45) Date of Patent: Apr. 22, 2025

(54) **DEDIFFERENTIATED CELL EXTRACT OF *BLETILLA* AND METHOD FOR WHITENING, ANTI-OXIDATION AND ANTI-WRINKLING APPLYING THE SAME, AND COSMETIC COMPRISING THE SAME**

(71) Applicant: CHLITINA INTELLIGENCE LIMITED, Tortola (VG)

(72) Inventors: Ruei-Ting Wang, Taipei (TW); Yi-Cian Lai, Taipei (TW); Wei-Ping Wang, Taipei (TW)

(73) Assignee: CHLITINA INTELLIGENCE LIMITED, Tortola (VG)

( * ) Notice: Subject to any disclaimer, the term of this patent is extended or adjusted under 35 U.S.C. 154(b) by 249 days.

(21) Appl. No.: 17/584,691

(22) Filed: Jan. 26, 2022

(65) Prior Publication Data

US 2022/0249360 A1  Aug. 11, 2022

(30) Foreign Application Priority Data

Feb. 9, 2021  (TW) .................. 110105056

(51) Int. Cl.
*A61K 8/9794* (2017.01)
*A61K 36/898* (2006.01)
*A61P 17/00* (2006.01)
*A61Q 19/02* (2006.01)
*A61Q 19/08* (2006.01)
*C12N 5/04* (2006.01)

(52) U.S. Cl.
CPC .......... *A61K 8/9794* (2017.08); *A61K 36/898* (2013.01); *A61P 17/00* (2018.01); *A61Q 19/02* (2013.01); *A61Q 19/08* (2013.01); *C12N 5/04* (2013.01); *A61K 2236/37* (2013.01); *A61K 2800/522* (2013.01)

(58) Field of Classification Search
CPC .................. A61K 2236/37; A61K 36/898
See application file for complete search history.

(56) References Cited

U.S. PATENT DOCUMENTS

2010/0267659 A1  10/2010  Sasaki et al.

FOREIGN PATENT DOCUMENTS

| CN | 103651121 A |   | 3/2014 | |
|---|---|---|---|---|
| CN | 105816507 A | * | 8/2016 | ........... A61K 31/352 |
| CN | 106832038 A | * | 6/2017 | ......... C08B 37/0003 |
| CN | 108030744 A |   | 5/2018 | |

OTHER PUBLICATIONS

Shi et al (Journal of Medicinal Plants Research, 2011, vol. 5, pp. 300-308) (Year: 2011).*
Wu et al (Journal of Food and Drug Analysis, 2010, vol. 18, pp. 279-289) (Year: 2010).*
CN-106832038-A (Google English Translation, downloaded on Nov. 2023) (Year: 2023).*
CN-105816507-A (Google English translation, downloaded on Nov. 2023) (Year: 2023).*
Li (Cosmetics and Toiletries, Apr. 2, 2013, TCM in Skin Whitening and Lightening: The Eternal Pursuit in East Asia, https://www.cosmeticsandtoiletries.com/formulas-products/article/21835131/tcm-in-skin-whitening-and-lightening-the-eternal-pursuit-in-east-asia) (Year: 2013).*
Tao et al (Mitochondrial DNA Part B Resources, Mar. 2020, vol. 5, pp. 1255-1256) (Year: 2020).*
China Patent Office, Office Action issued on Jun. 9, 2023 (CN202110352693.0).
Mingzhi Liu, Primarily studies on supercritical CO2 fluid extraction for components from Bletilla striata, 20110615, Journal of Central South University of Forestry & Technology.
Taiwan Patent Office, Office Action issued on Feb. 9, 2022 (TW110105056), Taiwan.

* cited by examiner

*Primary Examiner* — Mark V Stevens
(74) *Attorney, Agent, or Firm* — WPAT, PC (57) ABSTRACT

The present invention provides a *Bletilla* dedifferentiated cell extract by carbon dioxide supercritical extraction, which has triple cosmetic efficacies of whitening, anti-oxidation and anti-wrinkling, and the advantages of low skin irritation potential. The present invention further provides a method for whitening, anti-oxidation and anti-wrinkling by applying the extract by carbon dioxide supercritical extraction, and a cosmetic comprising the same so as to meet all the skin cosmetic needs of consumers in an all-round way.

16 Claims, 1 Drawing Sheet

DEDIFFERENTIATED CELL EXTRACT OF *BLETILLA* AND METHOD FOR WHITENING, ANTI-OXIDATION AND ANTI-WRINKLING APPLYING THE SAME, AND COSMETIC COMPRISING THE SAME

CROSS-REFERENCE TO RELATED APPLICATION

Pursuant to 35 U.S.C. § 119(a), this application claims the benefits of the priority to Taiwan Patent Application No. 110105056, filed on Feb. 9, 2021, which is incorporated by reference herein by its entirety.

BACKGROUND OF THE INVENTION

1. Field of the Invention

The present invention relates to a cosmetic ingredient and a method for whitening, anti-oxidation and anti-wrinkling applying the same, and a cosmetic comprising the same, especially the cosmetic ingredient comprising a plant extract.

2. Description of the Prior Arts

With the advancement of both technology and standard of living, people frequently interact with each other. In the process of social activities, people also pay more and more attention to their own appearance, and pursue the younger and healthier appearance, which brings a prosperous market for skin care.

There are all kinds of cosmetic products on the market. However, most of the products with stronger efficacy also irritate human skin more. For example, alpha hydroxy acids or A-aldehyde has excellent anti-wrinkle efficacy but brings a burning sensation upon application, and easily causes skin redness, dry skin and desquamation. Quinol has excellent whitening efficacy and can be used to lighten dark specks, but has the side effects of irritation and photosensitivity. L-vitamin C has excellent anti-oxidative efficacy, but is classified as acidic substance, which the irritation potential thereof is yet to be improved. Therefore, active ingredients with low skin irritation potential remain to be developed.

SUMMARY OF THE INVENTION

To solve the aforementioned problems, the present invention provides a dedifferentiated cell extract of a plant, obtained from supercritical extraction, wherein the plant is *Bletilla* plant in family Orchidaceae, and a solvent in the supercritical extraction is carbon dioxide.

The dedifferentiated cell extract of a plant of the present invention not only has three cosmetic efficacies: whitening, anti-oxidation and anti-wrinkling, but also has the advantage of low irritation potential.

The dedifferentiated cell of the present invention comprises a plant cell which is yet to differentiate or is dedifferentiated (dedifferentiation).

Preferably, the dedifferentiated cell is obtained from a seed (Seed), an embryoid (Embryoid), a somatic embryo (Somatic embryos), a protocorm (Protocorm), a protocorm-like body (Protocorm-like bodies, PLBs), a callus (Callus) or any combination thereof.

Preferably, the seed comprises an embryo (Embryo), a germ (Germ) or any combination thereof.

According to the present invention, the dedifferentiated cell extract of a plant has a cosmetic efficacy better than that of the differentiated cell extract, and is milder without skin or eye irritation potential.

In one embodiment, the dedifferentiated cell is obtained from a tissue culture from a seed by induction culture.

The medium for the induction culture and the method for the induction culture belong to known technologies, and can be adjusted according to the need, such as: the adoption of MS medium (Murashige & Skoog Medium) or B5 medium (B5 medium).

Preferably, the days for the induction culture are 40 days to 70 days, such as: 40 days, 50 days, 60 days or 70 days.

Preferably, the pH of an induction medium used in the induction culture is 5.7 to 5.9. More preferably, the pH thereof is 5.8.

In one embodiment, the induction medium comprises cane sugar and coconut water. Preferably, based on the total volume of the induction medium, the coconut water is in an amount of 10 volume percent to 15 volume percent, such as: 10 volume percent, 11 volume percent, 12 volume percent, 13 volume percent, 14 volume percent or 15 volume percent; and the cane sugar is in an amount of 20 g/L to 30 g/L, such as: 20 g/L, 22 g/L, 24 g/L, 26 g/L, 28 g/L or 30 g/L.

Preferably, the induction medium is further added with one selected from the group consisting of: 6-Benzylaminopurine (6-Benzylaminopurine, 6-BA), 2,4-dichlorophenoxyacetic acid (2,4-dichlorophenoxyacetic acid, 2,4-D) and Naphthaleneacetic acid (Naphthaleneacetic acid, NAA). More preferably, based on the total volume of the induction medium, 6-BA, 2,4-D or NAA is in an amount of 0.1 mg/mL to 5 mg/mL, such as: 0.1 mg/mL, 0.5 mg/mL, 1 mg/mL, 2 mg/mL, 3 mg/mL, 4 mg/mL or 5 mg/mL.

Preferably, the tissue culture is the somatic embryo, the protocorm, the protocorm-like body or the callus.

The culture medium and the culture method for the formation of the somatic embryo, the protocorm, the protocorm-like body or the callus from a seed by the induction culture can be adjusted according to the need. As the formation of the dedifferentiated cell by inducing the seed is a mature technology with operational stability, it is adopted by the present invention, but the present invention is not limited thereto.

Preferably, the dedifferentiated cell is obtained from the tissue culture further by proliferation culture.

The medium in the proliferation culture and the method for the proliferation culture can be adjusted according to the need.

In one embodiment, the medium in the proliferation culture is the same as the medium in the induction culture.

Preferably, the days for the proliferation culture are 30 days to 45 days, such as: 30 days, 35 days, 40 days or 45 days. The days for the proliferation culture is based on the growth state of the dedifferentiated cells, and the dedifferentiated cells are harvested when they reach confluence, or the quantity demanded is reached. In one embodiment, the suspension in a liquid medium in the proliferation culture is usually harvested after about 30 days. In another embodiment, by using a solid medium in the proliferation culture, the harvest is usually carried out after about 45 days.

Preferably, the proliferation culture is carried out in a dark environment.

Preferably, a subculture to a fresh proliferation medium in the proliferation culture is further carried out for every 15 days to 40 days, such as: 15 days, 20 days, 25 days, 30 days, 35 days or 40 days. If the dedifferentiated cell shows the signs of malnutrition, the subculture to a fresh proliferation medium can be carried out earlier and before the dedifferentiated cell reaches confluence or the quantity demanded is reached. If the cell number is high enough, the subculture or harvest can be carried out at any time as well. In one embodiment, by using a liquid medium for suspension in the proliferation culture, the harvest or subculture is usually carried out after about 15 days. In another embodiment, by using a solid medium in the proliferation culture, the harvest or subculture is usually carried out after about 35 days.

Although the supercritical extraction is a known technology, by adjusting parameters, the present invention extracts the targets with different properties. As proved by the experiments, the extract obtained in the present invention has unexpected efficacy: whitening, anti-oxidation, anti-wrinkling and low irritation potential. The extraction condition is elaborated as follows.

Preferably, the pressure of the supercritical extraction is 2000 psi to 7000 psi, such as: 2000 psi, 2500 psi, 3000 psi, 3500 psi, 4000 psi, 4500 psi, 5000 psi, 5500 psi, 6000 psi, 6500 psi or 7000 psi. More preferably, the pressure of the supercritical extraction is 4000 psi to 5000 psi.

Preferably, the temperature of the supercritical extraction is 40° C. to 60° C., such as: 40° C., 45° C., 50° C., 55° C. or 60° C.

Preferably, the time of the supercritical extraction is 5 hours to 10 hours, such as: 5 hours, 6 hours, 7 hours, 8 hours, 9 hours or 10 hours.

Preferably, the flow rate of the solvent used in the supercritical extraction is 4 L/min to 6 L/min, such as: 4 L/min, 4.2 L/min, 4.4 L/min, 4.6 L/min, 4.8 L/min, 5 L/min, 5.2 L/min, 5.4 L/min, 5.6 L/min, 5.8 L/min or 6 L/min.

In one embodiment, a co-solvent is further used in the supercritical extraction. Preferably, the co-solvent comprises methanol, ethanol, propanol, hexanol, propylene glycol, ethylene glycol, n-butanol, acetone, butanone, formic acid, acetic acid, ethyl acetate, cyclohexane, n-hexane, methyl chloride, dioxane, dimethyl sulfoxide, dimethyl acetamide, 2-Methoxyethanol, acetonitrile, sulfur hexafluoride, chlorine trifluoride, sulfur dioxide, carbon disulfide, tetrahydrofuran, propylene carbonate, chloroform, petroleum ether or any combination thereof. More preferably, the co-solvent is ethanol.

In one embodiment, the plant is *Bletilla formosana* (Hayata) Schltr (*Bletilla formosana* (Hayata) Schltr.).

According to the present invention, the effective concentration of the dedifferentiated cell extract of a plant is 0.005 weight percent or more. Preferably, the effective concentration is 0.005 weight percent to 30 weight percent, such as: 0.005 weight percent, 0.008 weight percent, 0.01 weight percent, 0.03 weight percent, 0.05 weight percent, 0.08 weight percent, 0.1 weight percent, 0.2 weight percent, 0.3 weight percent, 0.4 weight percent, 0.5 weight percent, 0.6 weight percent, 0.7 weight percent, 0.8 weight percent, 0.9 weight percent, 1 weight percent, 1.5 weight percent, 2 weight percent, 2.5 weight percent, 3 weight percent, 3.5 weight percent, 4 weight percent, 4.5 weight percent, weight percent, 5 weight percent, 10 weight percent, 15 weight percent, 20 weight percent, weight percent, 25 weight percent or 30 weight percent. More preferably, the effective concentration is the effective concentration for humans.

According to one particular embodiment of the present invention, after zebrafish embryos are treated with 10 mM of kojic acid (about 1421 µg/ml), the inhibition rate of melanin production is about 55%. After the treatment of 100 µg/ml of the dedifferentiated cell extract of *Bletilla* of the present invention, the inhibition rate of melanin production is about 66%, which means the dedifferentiated cell extract of *Bletilla* of the present invention, which has a concentration of one fourteenth of that of kojic acid, still has better inhibition rate of melanin production. The article of "The inhibition efficacy of kojic acid on melanin production and the therapeutic efficacy on various pigmentation disorders" published in 1994 disclosed that after 1% kojic acid was applied to male and female subjects, melanosis can be significantly inhibited. Therefore, the dedifferentiated cell extract of a plant of the present invention in a concentration of ¹⁄₁₄%, which is 0.07 weight percent, can demonstrate better whitening efficacy than that of kojic acid, and the effective concentration for human is 0.005 weight percent to 30 weight percent.

The present invention further provides a method for whitening, comprising applying an effective concentration of the dedifferentiated cell extract of a plant to a subject in need thereof. Preferably, the whitening comprises: suppressing or preventing melanin production, or degrading melanin.

The present invention further provides a method for anti-oxidation, comprising applying an effective concentration of the dedifferentiated cell extract of a plant to a subject in need thereof. Preferably, the anti-oxidation comprises: removing free radicals, reducing or ameliorating oxidative stress, or elevating gene expression of catalase or superoxide dismutase.

The present invention further provides a method for anti-wrinkling, comprising applying an effective concentration of the dedifferentiated cell extract of a plant to a subject in need thereof. Preferably, the anti-wrinkling comprises: elevating elastin gene expression, or suppressing or reducing matrix metalloproteinase production. More preferably, the matrix metalloproteinase is matrix metalloproteinase-1 (MMP-1).

Preferably, the dedifferentiated cell extract of a plant has low skin irritation potential. More preferably, the dedifferentiated cell extract of a plant has low eye irritation potential.

In one embodiment, the effective concentration indicates the concentration to show the beneficial efficacy of whitening, anti-oxidation or anti-wrinkling. Preferably, the beneficial efficacy of whitening comprises: suppressing or preventing melanin production, or degrading melanin; the beneficial efficacy of anti-oxidation comprises: removing free radicals, reducing or ameliorating oxidative stress, or elevating gene expression of catalase or superoxide dismutase; or the beneficial efficacy of anti-wrinkling comprises: elevating elastin gene expression, or suppressing or reducing matrix metalloproteinase production. More preferably, the matrix metalloproteinase is matrix metalloproteinase-1 (MMP-1).

In one embodiment, the method for whitening, anti-oxidation or anti-wrinkling is to apply the dedifferentiated cell extract of a plant to skin.

The present invention further provides a cosmetic, comprising the dedifferentiated cell extract of a plant, wherein the dosage form of the cosmetic comprises a solution, a suspension, a spray, a liquid lotion, a mousse, a gel, a lotion, a microemulsion, a cream, an ointment, a stick, a soap bar, a powder or a patch.

In one embodiment, the cosmetic comprises a facial cleanser, a makeup remover, a soap, a body wash, a shampoo, a toner, a face cream, a primer, a serum, a sunscreen, a tinted moisturizer, a liquid foundation, a foundation compact, a hand cream, a body lotion or a facial mask.

According to article 3 (1)(i) of Cosmetic Hygiene and Safety Act, revised on May 2 of the 107$^{th}$ year of the "Republic Era," the cosmetic of the present invention indicates that "products applied externally to the human body, teeth, or oral cavity mucous membranes, and used to moisturize hair and skin, stimulate the sense of smell, improve body odors, change appearance, or cleanse the body. However, this is not applicable to those that are regarded as drugs in accordance with other laws or regulations." Therefore, the cosmetic of the present invention comprises the cosmetic under article 3(1)(i) of Cosmetic Hygiene and Safety Act only, and does not comprise drugs in accordance with other laws or regulations.

According to 21 U.S.C. § 321(i), the cosmetic of the present invention indicates that "articles intended to be rubbed, poured, sprinkled, or sprayed on, introduced into, or otherwise applied to the human body or any part thereof for cleansing, beautifying, promoting attractiveness, or altering the appearance."

The present invention further provides a method for whitening, anti-oxidation or anti-wrinkling, comprising applying an effective amount of the cosmetic to a subject in need thereof, wherein the cosmetic comprises the dedifferentiated cell extract of a plant. Preferably, the whitening comprises: suppressing or preventing melanin production, or degrading melanin; the anti-oxidation comprises: removing free radicals, reducing or ameliorating oxidative stress, or elevating gene expression of catalase or superoxide dismutase; or the anti-wrinkling comprises: elevating elastin gene expression, or suppressing or reducing matrix metalloproteinase production.

In one embodiment, the effective amount indicates the amount to show the beneficial efficacy of whitening, anti-oxidation or anti-wrinkling. Preferably, the beneficial efficacy of whitening comprises: suppressing or preventing melanin production, or degrading melanin; the beneficial efficacy of anti-oxidation comprises: removing free radicals, reducing or ameliorating oxidative stress, or elevating gene expression of catalase or superoxide dismutase; or the beneficial efficacy of anti-wrinkling comprises: elevating elastin gene expression, or suppressing or reducing matrix metalloproteinase production. More preferably, the matrix metalloproteinase is matrix metalloproteinase-1 (MMP-1).

In one embodiment, the method for whitening, anti-oxidation or anti-wrinkling is to apply the cosmetic to skin.

To sum up, the dedifferentiated cell extract of a plant of the present invention has the advantage of whitening, anti-oxidation, anti-wrinkling and low skin irritation potential, which not only refrains the consumers from the uncomfortable feeling of skin and side effects, better meets the multiple needs of consumers for cosmetic care, but also reduces the complicated process to use multiple cosmetic care products with different cosmetic functions, owing to single product used to have one efficacy only. In other words, the present invention has three advantages of whitening, anti-oxidation and anti-wrinkling, which meets all the skin cosmetic needs of consumers in an all-round way and demonstrates great market competitiveness.

DETAILED DESCRIPTION OF THE PREFERRED EMBODIMENTS

The present invention is further explained through the following embodiments. A person having ordinary skill in the art can easily understand the advantages and efficacies achieved by the present invention. The present invention should not be limited to the contents of the embodiments. A person having ordinary skill in the art can make some improvement or modifications which are not departing from the spirit and scope of the present invention to practice or apply the content of the present invention.

Preparation Example 1: Callus of *Bletilla* Seed

In this experiment, the seeds of *Bletilla formosana* (Hayata) Schltr. were used for induction culture to obtain callus. First, the outer coverings of the pods of the capsules, which were grown for 2.5 months after pollination, were cleaned with detergent, disinfected with 75% alcohol for 1 minute, and then disinfected with 1% to 3% sodium hypochlorite solution for 30 minutes. After cleaning with sterile water for three times in the laminar air flow hood, the seeds were taken out and cultured in an induction medium with a pH of 5.8 for 50 days to 70 days to obtain callus; wherein the ingredients of the induction medium were shown in Table 1; wherein one or two selected from 6-BA, 2,4-D and NAA were added to the induction medium and the respective addition amount was 0.1 to 5 mg/L. The obtained callus was mixed for use.

TABLE 1

| induction medium | |
|---|---|
| Ingredients | Amount (mg/L) |
| $NH_4NO_3$ | 1650 |
| $KNO_3$ | 1900 |
| $MgSO_4 \cdot 7 H_2O$ | 370 |
| $CaCl_2 \cdot 2 H_2O$ | 440 |
| $KH_2PO_4$ | 170 |
| $ZnSO_4 \cdot 7 H_2O$ | 8.6 |
| $MnSO_4 \cdot H_2O$ | 16.9 |
| $CuSO_4 \cdot 5 H_2O$ | 0.025 |
| KI | 0.083 |
| $CoCl_2 \cdot 6 H_2O$ | 0.025 |
| $H_3BO_3$ | 62 |
| $Na_2MoO_4 \cdot 2 H_2O$ | 0.25 |
| $Na_2EDTA$ | 37.3 |
| $FeSO_4 \cdot 7 H_2O$ | 27.8 |
| Pyridoxine hydrochloride (Vitamin B6) | 0.5 |
| Thiamine hydrochloride (Vitamin B1) | 0.400 |
| Nicotinic acid (Vitamin B3) | 0.500 |
| Glycine | 1.000 |
| Myoinositol | 100 |
| Agar | 7000 |
| Coconut water | 100 to 150 ml/L |
| Sucrose | 20000 |
| 6-BA/2,4-D/NAA | 0.1 to 10 |

Preparation Example 2 *Bletilla* Dedifferentiated Cell

The callus from Preparation example 1 was inoculated into a fresh solid proliferation medium, and the proliferation culturing was carried out at room temperature of 25° C. in a dark environment to obtain a tissue culture, which comprised *Bletilla* dedifferentiated cell. During the process of proliferation culturing, part of the tissue culture was taken out for subculturing at Day 35, and the rest of the tissue culture continued for the proliferation culturing or was harvested at the same time. In addition, the proliferation medium is the same as the aforementioned induction medium.

Preparation Example 3: *Bletilla* Extract

Example 1: Supercritical Carbon Dioxide Extraction of the Dedifferentiated Cells The tissue culture, which comprised *Bletilla* dedifferentiated cells and was cultured for 35 days to 45 days from Preparation example 2, was subjected to lyophilization and then pulverized to obtain a cell lyophilized powder, wherein the supercritical carbon dioxide fluid served as a solvent, and the extraction was carried out at the pressure between 4000 psi to 5000 psi and the temperature between 40° C. to 60° C. with the flow rate of carbon dioxide fluid between 4 L/min to 6 L/min for 5 hours to 10 hours to obtain an ointment-like supercritical carbon dioxide fluid extract, which is the supercritical carbon dioxide extract of *Bletilla* dedifferentiated cells.

Comparative Example 1: Ethanol Extract of the Dedifferentiated Cells

The tissue culture, which comprised *Bletilla* dedifferentiated cells and was cultured for 35 days to 45 days from Preparation example 2, was subjected to lyophilization and then pulverized to obtain a cell lyophilized powder. The cell lyophilized powder was mixed with 50% ethanol aqueous solution at a weight-to-volume ratio of 1:50, agitated by ultrasonic waves for 1 hour, and the obtained extract was filtered and concentrated under reduced pressure, and then lyophilized to obtain an ethanol extract of *Bletilla* dedifferentiated cells.

Comparative Example 2: Ethanol Extract of Medicinal Herbs

A dried *Bletilla* root was provided for pulverization to obtain a *Bletilla* powder. The *Bletilla* powder was mixed with 50% ethanol aqueous solution at a weight-to-volume ratio of 1:50, agitated by ultrasonic waves for 1 hour, and the obtained extract was filtered and concentrated under reduced pressure, and then lyophilized to obtain an ethanol extract of medicinal herbs.

Analysis 1: Analysis by High Performance Liquid Chromatography

The high performance liquid chromatography used in this experiment was Waters 600; the chromatography column was C-18, inertsil 5 ODS, 4.6*250 mm; the wavelength was UV 200 nm to 400 nm; the flow rate was 1.0 mL/min; Solution A serving as the mobile phase was $H_2O$ (0.1% phosphoric acid), Solution B was acetonitrile, the gradient elution mode was 0 to 15 minutes (95-85: 5-15), 15 to 50 minutes (85-40: 15-60), 50 to 55 minutes (40-95: 60-5), 55 to 60 minutes (95:5), the injection volume: 20 μL; the temperature of the column was room temperature.

Figure 1:
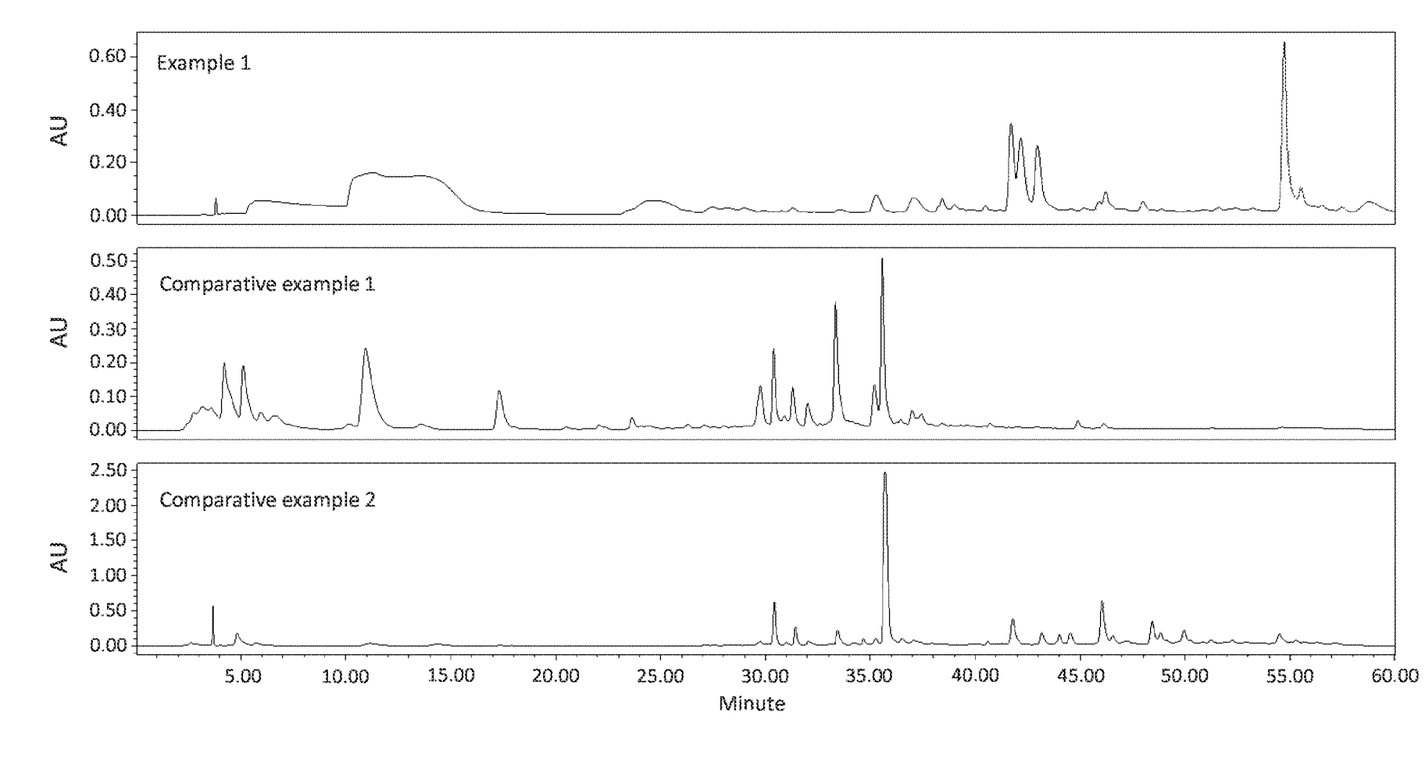
FIG. 1 is the analysis charts of different extracts by high performance liquid chromatography.

The solvent for Example 1 was ethanol, and the solvent for both Comparative example 1 and Comparative example 2 was water. 10 mg of each of Example 1, Comparative example 1 and Comparative example 2 was dissolved in 1 mL of the solvent to obtain a sample stock solution, which was subjected to ultrasonic agitation for dissolution and then filtered for analysis. The results were shown in FIG. 1; wherein FIG. 1 showed that the ingredients of Example 1, Comparative example 1 and Comparative example 2 were different. According to the peaks at about 40 to 45 minutes and 55 minutes of Example 1, Example 1 comprised more ingredients with low polarity.

Analysis 2: Analysis of Total Polyphenol Content

The solvent for Example 1 was ethanol, and the solvents for both Comparative example 1 and Comparative example 2 were water. 10 mg of each of Example 1, Comparative example 1 and Comparative example 2 was dissolved in 1 mL of the solvent to obtain a sample stock solution. 100 μL of the sample stock solution was 10-fold diluted with the solvent, added with 2 mL of water and 0.25 mL of 1N Folin-Ciocalteu reagent, mixed evenly and standing still for 5 minutes, added with 0.25 mL of 20% $Na_2CO_3$ solution and mixed evenly, and subjected to reaction for 2 hours. The absorbance value at 750 nm was measured by FlexStation®3 Multi-Mode Microplate Reader. Gallic acid was used as a reference standard, and the gallic acid equivalent (Gallic acid equivalent) amount (mg) comprised in each group per gram was the total polyphenol content, and the results were shown in Table 1.

TABLE 2

Total polyphenol content in each group

| Group | Total polyphenol content (mg gallic acid eq./g) |
| --- | --- |
| Example 1 | 23.74 ± 0.75 |
| Comparative example 1 | 25.07 ± 0.97 |
| Comparative example 2 | 26.10 ± 0.62 |

According to Table 2, the total polyphenol contents among Example 1, Comparative example 1 and Comparative example 2 were similar; wherein the total polyphenol content measured in Example 1 was the lowest.

Test 1: Whitening Efficacy in Cell Test (1) Cytotoxicity Test for Mouse Melanocytes Mouse melanocytes of B16-F10 (ATCC® CRL-6475™) cultured in DMEM culture medium were seeded into a 96-well culture dish at a density of $5\times10^3$ cells per well, and were cultured for 24 hours to allow them to adhere to the culture dish. The DMEM culture medium in each control group was added with a solvent, wherein the solvent for Example 1 was DMSO, and the control group for Example 1 was added with the same amount of DMSO, which was 0.5% DMSO based on the culture medium, as that in Example 1 for comparison. In Comparative example 1 and Comparative example 2, water served as the solvent, and the control groups for the comparative examples were also added with the same amount of water, which was 0.25% water based on the culture medium, as that in each group of Comparative example 1 and Comparative example 2 for comparison. Each experimental group was added with different concentrations of Example 1, Comparative example 1 and Comparative example 2, cultured for 48 hours, and then added with 500 μg/mL MTT solution, and cultured at 37° C. for 2 hours. The MTT solution was removed, and 200 μL DMSO was added to dissolve the crystals, and the absorbance value at 570 nm was measured. Each group was repeated in duplicate, and the viability percentage of each control group served as the standard, that is, the viability percentage thereof was 100%. The relative cell viability percentages of the experimental groups were calculated, and the results were shown in Table 3.

TABLE 3

Results of the relative cell viability percentages of the experimental groups

| Group | Concentration (μg/mL) | Average (%) |
|---|---|---|
| Example 1 | 250 | 100.5 |
|  | 125 | 104.4 |
|  | 62.5 | 107.2 |
|  | 31.25 | 114.3 |
| Comparative example 1 | 250 | 94.5 |
|  | 125 | 98.8 |
|  | 62.5 | 104.0 |
|  | 31.25 | 108.2 |
| Comparative example 2 | 250 | 99.5 |
|  | 125 | 104.6 |
|  | 62.5 | 109.4 |
|  | 31.25 | 104.7 |

According to the results shown in Table 3, the cell viability percentages of the mouse melanocytes in each group were similar, and were all more than 90%.

(2) Melanin Production Inhibition Test for Mouse Melanocytes

The aforementioned mouse melanocytes were seeded into a 6-well culture dish at a density of $3 \times 10^4$ cells per well, and cultured for 24 hours to allow them to adhere to the culture dish. After the DMEM culture medium was refreshed, all groups, except the control group, were added with 100 nM of α-melanocyte-stimulating hormone (α-Melanocyte-stimulating hormone, α-MSH). Each negative control group was further added with a solvent, wherein the solvent for Example 1 was DMSO, and the negative control group for Example 1 was added with the same amount of DMSO, which was 0.4% DMSO based on the culture medium, as that in Example 1 for comparison. In Comparative example 1 and Comparative example 2, water served as the solvent, and the negative control groups for the comparative examples were also added with the same amount of waters, which was 0.2% water based on the culture medium, as that in each group of Comparative example 1 and Comparative example 2 for comparison. The positive control group was added with arbutin (Arbutin). Each group was cultured for 48 hours, washed once with PBS, and added with trypsin to make the mouse melanocytes detach. The mouse melanocytes were collected, subjected to centrifugation to remove the supernatant, added with 1M NaOH and 10% DMSO, and heated in a dry bath at 80° C. for 2 hours. The absorbance value at 400 nm was measured. Each group was repeated in duplicate, and the melanin amount of each negative control group served as the standard, that is, the melanin amount thereof was 100%. The relative melanin amounts of the rest of the groups were calculated, and the results were shown in Table 4, wherein the comparison target in T-test was the respective negative control group.

TABLE 4

Results of the relative melanin amount in each group

| Group | Concentration | Average (%) | T-test |
|---|---|---|---|
| Control group | N/A | 52.6 | P < 0.05 |
| Positive control group | 10 mM | 26.2 | P < 0.05 |
| Example 1 | 200 μg/mL | 49.4 | P < 0.001 |
|  | 50 μg/mL | 74.0 | P < 0.05 |
| Comparative example 1 | 200 μg/mL | 79.7 | P < 0.05 |
|  | 50 μg/mL | 88.6 | No significant difference |
| Comparative example 2 | 20 μg/mL | 82.2 | P < 0.05 |
|  | 50 μg/mL | 78.8 | P < 0.05 |

According to the results shown in Table 4, the melanin amount in Example 1 at the concentration of 200 μg/mL was reduced to 49.4%, while the melanin amount in Example 1 at the concentration of 50 μg/mL was reduced to 74.0%, which indicated that the inhibition rate of the melanin production in Example 1 was about 25% to 50%. In contrast, the inhibition rates of melanin production in Comparative example 1 and Comparative example 2 were only about 10% to 20%. Therefore, Example 1 had the efficacy to inhibit the melanin production that was significantly better than those in Comparative example 1 and Comparative example 2.

Second, the viability percentage of mouse melanocytes in each group was similar, so the efficacy to inhibit the melanin production in Example 1 did not result from cytotoxicity. Finally, the total polyphenol contents in Example 1, Comparative example 1 and Comparative example 2 were similar, so the better efficacy to inhibit the melanin production in Example 1 was irrelevant to the total polyphenol content as well.

Test 2: Whitening Efficacy in Zebrafish Experiment

The wild-type zebrafish were stimulated to spawn, and the eggs spawned within one hour were collected. Upon 9 hours after fertilization, the embryos were screened by microscope to confirm the developmental state after fertilization. Each group had 12 fish embryos. The E3 culture medium, which was the zebrafish embryo culture medium, served as the control group. The positive control group was added with kojic acid (Kojic acid). Each experimental group was added with Example 1, Comparative example 1 and Comparative example 2, respectively. As zebrafish embryos produced melanin within 24 hours after fertilization, the treatment finished before the production of melanin, and the melanin production state in the hatched fish was observed upon 72 hours after fertilization. First, the fish was anesthetized and placed on a flat surface. The photo was taken from a top view, and the melanin plaques were analyze by the software of ImageJ. The intensity of the melanin plaque in the control group served as the standard, that is, the melanin amount thereof was 100%. The relative melanin amounts of the rest of the groups were calculated. The results were shown in Table 5.

TABLE 5

Results of the relative melanin amount in each group

| Group | Concentration | Average (%) | Inhibition rate |
|---|---|---|---|
| Positive control group | 10 mM | 48.6% ± 9.3 | 51.40% |
| Example 1 | 100 μg/mL | 33.40% ± 6.2 | 66.60% |
| Comparative example 1 | 100 μg/mL | 65.95% ± 9.3 | 34.05% |
| Comparative example 2 | 100 μg/mL | 68.9% ± 5.9 | 31.10% |

According to Table 5, the inhibition rate of melanin production for zebrafish in Example 1 at the concentration of 100 μg/mL reached 66.60%, which was better than 34.05% in Comparative example 1 at the same concentration and 31.10% in Comparative example 2 at the same concentration. Besides, Example 1 at the concentration of 100 μg/mL, which was converted to 0.1 g/L, had the inhibition rate of 66.60%. The positive control group at the concentration of 10 mM, which was converted to 1.42 g/L, had the inhibition rate of 51.40%. Therefore, Example 1 not only had a significantly lower concentration, but also demonstrated better inhibition efficacy on melanin production than that of commercially available kojic acid.

Test 3: DPPH Assay for Antioxidant

In a 96-well culture dish, the blank group for each experimental group (the Example and the Comparative examples) was added with 50 μL of the solvent, wherein the solvent for Example 1 was DMSO, and the solvents for both Comparative example 1 and Comparative example 2 were water. The experimental groups were added with 50 μL of the serial dilution solutions of Example 1, Comparative example 1 and Comparative example 2. Each group was repeated at least three times. Before the addition of 150 μL of DPPH solution, the absorbance value at 515 nm was measured and served as the background value, and then DPPH was added and mixed evenly for reaction at room temperature for 20 minutes. The absorbance value at 515 nm was measured, and the concentration upon the DPPH scavenging rate reaching 50% ($IC_{50}$) was calculated, which was the 50% DPPH scavenging concentration, wherein DPPH scavenging rate=[(A−A0)−(B−B0)/(A−A0)]×100%; A is the absorbance value of the blank group; B is the absorbance value of the experimental group; A0 is the background absorbance value of the blank group; B0 is the background absorbance value of the experimental group or the control group. The results were shown in Table 6.

TABLE 6

| 50% DPPH scavenging concentration | |
|---|---|
| Group | $IC_{50}$ (μg/mL) |
| Example 1 | 1079.6 ± 85.7 |
| Comparative example 1 | 1376.4 ± 44.2 |
| Comparative example 2 | 1223.0 ± 149.4 |

According to Table 6, the 50% DPPH scavenging concentrations of the three groups were similar, so the antioxidant capacities of the three groups were similar.

Test 4: ABTS Free Radical Scavenging Experiment for Antioxidants

In a 96-well culture dish, the blank group for each experimental group (the Example and the Comparative examples) was added with 100 μL of the solvent, wherein the solvent for Example 1 was DMSO, and the solvents for both Comparative example 1 and Comparative example 2 were water. The experimental groups were added with 100 μL of the serial dilution solutions of Example 1, Comparative example 1 and Comparative example 2. Each group was repeated at least in triplicate. Before the addition of 100 μL of 280 μM ABTS (2,2'-azino-bis(3-ethylbenzothiazoline-6-sulfonic acid) solution, the absorbance value at 734 nm was measured and served as the background value, and then the ABTS solution was added and mixed evenly for reaction at 25° C. for 15 minutes. The absorbance value at 734 nm was measured, and the concentration upon the ABTS free radical scavenging rate reaching 50% ($IC_{50}$) was calculated, and the calculation formula was the same as that in Test 3. The results were shown in Table 7.

TABLE 7

| 50% ABTS free radical scavenging concentration | |
|---|---|
| Group | $IC_{50}$ (μg/mL) |
| Example 1 | 60.69 ± 0.50 |
| Comparative example 1 | 39.01 ± 0.62 |
| Comparative example 2 | 55.81 ± 1.80 |

According to Table 7, the ABTS free radical scavenging efficacy of Example 1 was not better than those of Comparative example 1 and Comparative example 2.

Test 5: Reactive Oxygen Species Metabolism Experiment for Human Fibroblasts (1) Cytotoxicity Test for Human Fibroblasts Human fibroblasts of CCD-966SK (ATCC® CRL-1881™) cultured in MEM culture medium were seeded into a 96-well culture dish at a density of $5×10^3$ cells per well, and were cultured for 24 hours to allow them to adhere to the culture dish.

The MEM culture medium in each control group was added with a solvent, wherein the solvent for Example 1 was DMSO, and the control group for Example 1 was added with the same amount of DMSO, which was 1% DMSO based on the culture medium, as that in Example 1 for comparison. Each experimental group was added with different concentrations of Example 1, cultured for 24 hours, and then added with 500 μg/mL MTT solution, and cultured at 37° C. for 2 hours. The MTT solution was removed, and 200 μL DMSO was added to dissolve the crystals, and the absorbance value at 570 nm was measured. Each group was repeated in triplicate, and the cell viability percentage of the control group served as the standard, that is, the viability percentage thereof was 100%. The relative cell viability percentages of the experimental groups were calculated, and the results were shown in Table 8.

TABLE 8

| The results of the relative cell viability percentages of the experimental groups | | | |
|---|---|---|---|
| Group | Concentration | Average (%) | T-test |
| Example 1 | 500 μg/mL | 28.9 | P < 0.001 |
| | 250 μg/mL | 92.4 | No significant difference |
| | 125 μg/mL | 99.5 | No significant difference |
| | 62.5 μg/mL | 100.0 | No significant difference |

According to Table 8, when the concentration of Example 1 was below 250 μg/mL, the cell viability percentages were all more than 90%.

(2) Reactive Oxygen Species Metabolism Experiment for Human Fibroblasts

The aforementioned human fibroblasts were seeded into a 96-well culture dish at a density of $5×10^3$ cells per well, cultured for 24 hours to allow them to adhere to the culture dish, added with 500 μM H2O2 for reaction for hours, and then refreshed with fresh MEM culture medium. The MEM culture medium of the control group was added with a solvent, wherein the solvent for Example 1 was DMSO, and the control group for Example 1 was added with the same amount of DMSO, which was 0.5% DMSO based on the culture medium, as that in Example 1 for comparison. All experimental groups were added with different concentrations of Example 1. Each group was cultured for 24 hours, and the cells were divided into two parts: one was washed twice with PBS, and added with a solution containing 10 µM DCFH-DA fluorescent dye for reaction at 37° C. for 30 minutes. The DCF fluorescence intensity was measured, which represented the amount of cellular reactive oxygen species. Each group was repeated in duplicate, and the fluorescence intensity of the control group served as the standard, that is, the amount of cellular reactive oxygen species thereof was 100%. The relative amount of cellular reactive oxygen species of the experimental groups were calculated. Another one was subjected to the cytotoxicity test for human fibroblasts, which was added with 500 µg/mL MTT solution for reaction at 37° C. for 3 hours. The absorbance value at 570 nm was measured and represented cell viability. Each group was repeated in duplicate. The results were shown in Table 9, wherein the comparison target in T-test was the control group.

TABLE 9

The results of the relative cell viability percentages and the relative DCF fluorescence intensities of the experimental group

| Group | Concentration | Relative cell viability percentage Average (%) | Relative DCF fluorescence intensity Average (%) | T-test |
|---|---|---|---|---|
| Example 1 | 250 µg/mL | 101.0 | 65.0 | P < 0.05 |
| | 125 µg/mL | 102.4 | 91.1 | No significant difference |
| | 62.5 µg/mL | 96.0 | 107.0 | No significant difference |

According to Table 9, the cell viability percentage at each concentration was similar, and the DCF fluorescence intensity at the concentration of 250 µg/mL was significantly lower than that in the control group, and the oxidative pressure was inhibited by nearly 35%, which indicated that Example 1 can indeed reduce reactive oxygen species and reduce or ameliorate oxidative stress.

Test 6: Gene Expression Experiment of the Catalase and the Superoxide Dismutase in Human Fibroblasts The aforementioned human fibroblasts were seeded into a 6-well culture dish at a density of $1.5 \times 10^5$ cells per well, cultured for 24 hours to allow them to adhere to the culture dish, and then refreshed with fresh MEM culture medium. The MEM culture medium of the control group was added with a solvent, wherein the solvent for Example 1 was DMSO, and the control group for Example 1 was added with the same amount of DMSO, which was 0.4% DMSO based on the culture medium, as that in Example 1 for comparison. The experimental group was added with 200 µg/mL Example 1 for reaction for 24 hours, and washed once with PBS. The cells were collected and subjected to RNA purification. The cDNA was obtained by reverse transcription and subjected to real-time quantitative polymerase chain reaction (real-time PCR). The gene expression levels of the catalase and the superoxide dismutase in the control group served as the standard for calculating the relative gene expression levels of the catalase and the superoxide dismutase in the human fibroblasts treated with Example 1. In this experiment, Quick-RNA™ Miniprep Kit was adopted for RNA purification, Magic RT cDNA synthesis kit was adopted to obtain cDNA by reverse transcription, and KAPA SYBR Fast qPCR Master Mix was adopted to carry out PCR. The results were shown in Table 10.

TABLE 10

The relative gene expression level folds of the catalase and the superoxide dismutase after the treatment of Example 1

| Group | Concentration | Catalase (fold) | Superoxide dismutase (fold) |
|---|---|---|---|
| Example 1 | 200 µg/mL | 2.3 ± 0.22 | 2.0 ± 0.26 |

According to Table 10, the relative gene expression levels of both the catalase and the superoxide dismutase in Example 1 were the double of those in the control group, which indicated that Example 1 can indeed improve the gene expression of the catalase and the superoxide dismutase. Example 1 can increase the cell antioxidant capacity of human fibroblast, resist environmental pathogenic factors, and promote the defending capacity of skin.

Test 7: The Elastin Gene (ELN2) Expression in Anti-Wrinkle Experiment

The aforementioned human fibroblasts were seeded into a 6-well culture dish at a density of $1.5 \times 10^5$ cells per well, cultured for 24 hours to allow them to adhere to the culture dish, and then refreshed with fresh MEM culture medium. The MEM culture medium of the control group was added with a solvent, wherein the solvent for Example 1 was DMSO, and the control group for Example 1 was added with the same amount of DMSO, which was 0.4% DMSO based on the culture medium, as that in Example 1 for comparison. The experimental group was added with 200 µg/mL Example 1 for reaction for 24 hours, and washed once with PBS. The cells were collected and subjected to RNA purification. The cDNA was obtained by reverse transcription and subjected to real-time quantitative polymerase chain reaction. The gene expression levels of the elastin gene (ELN2) in the control group served as the standard for calculating the relative gene expression levels in the human fibroblasts treated with Example 1. In this experiment, Quick-RNA™ Miniprep Kit was adopted for RNA purification, Magic RT cDNA synthesis kit was adopted to obtain cDNA by reverse transcription, and KAPA SYBR Fast qPCR Master Mix was adopted to carry out PCR. The results were shown in Table 11.

TABLE 11

The relative gene expression level folds of the elastin gene in Example 1

| Group | Concentration | Elastin gene (fold) |
|---|---|---|
| Example 1 | 200 µg/mL | 1.8 ± 0.26 |

According to Table 11, the relative gene expression level of the elastin gene in Example 1 was 1.8 folds of that of the control group, which indicated that Example 1 can indeed increase the structural proteins in skin so as to achieve the anti-wrinkle efficacy and promote the defending capacity of skin.

Test 8: Matrix Metalloproteinase-1 (MMP-1) Protein for Anti-Wrinkle Experiment (1) Cytotoxicity Test of Human Fibroblasts Human fibroblasts of Hs68 (ATCC® CRL-1635™) cultured in DMEM culture medium were seeded into a 96-well culture dish at a density of $1 \times 10^4$ cells per well, and were cultured for 24 hours to allow them to adhere to the culture dish. The DMEM culture medium in the control group was added with a solvent, wherein the solvent for Example 1 was DMSO, and the control group for Example 1 was added with the same amount of DMSO, which was 0.2% DMSO based on the culture medium, as that in Example 1 for comparison. In Comparative example 1 and Comparative example 2, water served as the solvent, and the control groups for the comparative examples were also added with the same amount of waters, which was 10% water based on the culture medium, as that in each group of Comparative example 1 and Comparative example 2 for comparison. The experimental groups were added with 20 μg/mL Example 1, 1000 μg/mL Comparative example 1 and 1000 μg/mL Comparative example 2, cultured for 24 hours, and then added with 500 μg/mL MTT solution, and cultured at 37° C. for 2 hours. The MTT solution was removed, 200 μL DMSO was added to dissolve the crystals, and the absorbance value at 570 nm was measured. The viability percentage of the control group served as the standard, that is, the viability percentage thereof was 100%. The relative cell viability percentages of the experimental groups were calculated, and the results were shown in Table 12.

According to Table 12, Example 1 at the concentration of 20 μg/mL, and Comparative examples 1 and 2 at the concentration of 1000 μg/mL showed high viability percentages.

(2) MMP-1 Assay in Human Fibroblasts

The aforementioned human fibroblasts were seeded into a 96-well culture dish at a density of $1\times10^4$ cells per well, cultured for 24 hours to allow them to adhere to the culture dish, refreshed with fresh DMEM culture medium, and then added with 10 ng/mL TNF-α. The DMEM culture medium of the control group was added with a solvent, wherein the solvent for Example 1 was DMSO, and the control group for Example 1 was added with the same amount of DMSO, which was 0.2% DMSO based on the culture medium, as that in Example 1 for comparison. In Comparative example 1 and Comparative example 2, water served as the solvent, the control groups for the comparative examples were also added with the same amount of waters, which was 10% water based on the culture medium, as that in each group of Comparative example 1 and Comparative example 2 for comparison. The experimental groups were added with 20 μg/mL Example 1, 1000 μg/mL Comparative example 1 and 1000 μg/mL Comparative example 2 for reaction for 18 hours. The cell culture supernatant was harvested and subjected to enzyme-linked immunosorbent assay (ELISA) to analyze the amount of MMP-1. The amount of MMP-1 of the control group served as the standard, that is, the amount of MMP-1 thereof was 100%. The relative amounts of MMP-1 of the experimental groups were calculated. The results were shown in Table 12.

TABLE 12

The results of the relative cell viability percentages and the relative amounts of MMP-1 in the experimental groups

| Group | Concentration (μg/mL) | Relative cell viability percentage Average (%) | MMP-1 Average (%) | Inhibition rate (%) |
|---|---|---|---|---|
| Example 1 | 20 | 101.7 ± 0.8 | 49.2 ± 6.6 | 50.8 |
| Comparative example 1 | 1000 | 101.3 ± 1.5 | 135.7 ± 9.7 | −35.7 |
| Comparative example 2 | 1000 | 103.2 ± 2.1 | 110.3 ± 19.6 | −10.3 |

According to Table 12, Example 1 at the concentration of 20 μg/mL demonstrated the inhibition efficacy on MMP-1 production. In contrast, Comparative example 1 and Comparative example 2 even at 50 folds of the concentration still showed no inhibition efficacy, or even promote MMP-1 production. Therefore, Example 1 can inhibit the degradation of structural proteins in skin so as to achieve the anti-wrinkle efficacy and promote the defending capacity of skin, and such inhibition efficacy did not result from cytotoxicity.

Test 9: Safety Analysis (1) Eye Irritation Assessment Experiment

In this experiment, the reconstructed human corneal cell (RhCE) model was adopted and tested in accordance with the OECD TG492 specification. The kit adopted was EpiOcula™ Eye Irritation Test (OCL-200-EIT) certified by ECVAM (the European Reference Laboratory for alternatives to animal testing).

In this experiment, the negative control group was added with water, and the positive control group was added with methyl acetate (methyl acetate). Each experimental group was added with 50 mg of Example 1 and Comparative example 1, respectively, cultured for 6 hours, refreshed with fresh culture medium, cultured for another 18 hours, added with 1 mg/mL MTT solution for reaction for 3 hours, and then added with isopropanol (isopropanol) to dissolve the crystals. The absorbance value at 570 nm was measured. In this experiment, the absorbance value of the negative control group served as the standard, that is, the absorbance value of the negative control group was 100%, and the rest of the groups had an absorbance value less than 60% will be identified as being eye irritating. The results were shown in Table 13.

TABLE 13

The assessment results of the relative cell viability percentages and eye irritations in each group

| Group | Relative cell viability percentage (%) | Eye irritation |
|---|---|---|
| positive control group | 47.6% ± 4.17 | O |
| Example 1 | 73.0% ± 1.20 | X |
| Comparative example 1 | 5.7% ± 0.33 | O |

According to Table 13, in the condition that same amounts of both Example 1 and Comparative example 1 were added, Example 1 was not eye irritating, and Comparative example 1 was eye irritating, so Example 1 had low irritation potential and the application thereof was safer for the human body.

(2) Skin Irritation Assessment Experiment

In this experiment, the reconstructed human epidermis (RhE) skin model was adopted and tested in accordance with the OECD TG439 specification. The kit adopted was In Vitro EpiDerm™ Skin Irritation Test (EPI-200-SIT) certified by ECVAM.

The negative control group was added with DPBS solution, and the positive control group was added with 5% SDS aqueous solution. The experimental groups were added with 25 mg of Example 1 and Comparative example 1, respectively, cultured for 1 hour, refreshed with fresh culture medium, cultured for another 42 hours, added with 1 mg/mL MTT solution for reaction for 3 hours, and then added with isopropanol to dissolve the crystals. The absorbance value at 570 nm was measured. In this experiment, the absorbance value of the negative control group served as the standard, that is, the absorbance value of the negative control group was 100%, and the rest of the groups having an absorbance value less than 50% will be identified as being skin irritating. The results were shown in Table 14.

TABLE 14

The assessment results of the relative cell viability percentages and skin irritations in each group

| Group | Relative cell viability percentage (%) | Skin irritation |
| --- | --- | --- |
| positive control group | 1.6 ± 0.14 | O |
| Example 1 | 98.0 ± 0.30 | X |
| Comparative example 1 | 98.4 ± 0.59 | X |

According to Table 14, in the condition that same amounts of both Example 1 and Comparative example 1 were added, the relative cell viability percentages thereof were similar and similar to the 100% of the negative control group, so Example 1 was not skin irritating and suitable for topical application.

To sum up, the dedifferentiated cell extract of a plant of the present invention not only has triple cosmetic efficacies of whitening, anti-oxidation and anti-wrinkling, but also has the advantages of low skin and eye irritation potential.

What is claimed is:

1. An extract mixture, comprising a dedifferentiated cell extract of a plant obtained from supercritical extraction, wherein based on a total weight of the extract mixture, the dedifferentiated cell extract of the plant is in an amount of 0.005 weight percent to 30 weight percent;
   the plant is *Bletilla* plant in family Orchidaceae;
   a solvent used in the supercritical extraction is carbon dioxide; and
   the dedifferentiated cell is obtained from a callus.

2. The extract mixture as claimed in claim 1, wherein the callus is obtained from a seed by induction culture.

3. The extract mixture as claimed in claim 1, wherein the dedifferentiated cell is obtained from the callus by proliferation culture: the time for the proliferation culture is 30 days to 45 days; or the pH of a proliferation medium used in the proliferation culture is 5.7 to 5.9.

4. The extract mixture as claimed in claim 1, wherein the supercritical extraction is carried out at a pressure of 2000 psi to 7000 psi, a temperature of 40° C.' to 60° C.; and a flow rate of the solvent of 4 L/min to 6 L/min for a time of 5 hours to 10 hours.

5. The extract mixture as claimed in claim 1, wherein a co-solvent is further used in the supercritical extraction.

6. The extract mixture as claimed in claim 1, wherein the plant is *Bletilla formosana* (Hayata) Schltr.

7. A method for whitening, anti-oxidation or anti-wrinkling, comprising applying the extract mixture as claimed in claim 1 to a subject in need thereof.

8. A method for whitening, anti-oxidation or anti-wrinkling, comprising applying the extract mixture as claimed in claim 3 to a subject in need thereof.

9. A method for whitening, anti-oxidation or anti-wrinkling, comprising applying the extract mixture as claimed in claim 3 to a subject in need thereof.

10. A method for whitening, anti-oxidation or anti-wrinkling, comprising applying the extract mixture as claimed in claim 4 to a subject in need thereof.

11. A method for whitening, anti-oxidation or anti-wrinkling, comprising applying the extract mixture as claimed in claim 5 to a subject in need thereof.

12. A method for whitening, anti-oxidation or anti-wrinkling, comprising applying the extract mixture as claimed in claim 6 to a subject in need thereof.

13. The method as claimed in claim 7, wherein the whitening comprises: suppressing or preventing melanin production, or degrading melanin; the anti-oxidation comprises: removing free radicals, reducing or ameliorating oxidative stress, or elevating gene expression of catalase or superoxide dismutase; or the anti-wrinkling comprises: elevating elastin gene expression, or suppressing or reducing matrix metalloproteinase production.

14. The method as claimed in claim 10, wherein the whitening comprises: suppressing or preventing melanin production, or degrading melanin; the anti-oxidation comprises: removing free radicals, reducing or ameliorating oxidative stress, or elevating gene expression of catalase or superoxide dismutase; or the anti-wrinkling comprises: elevating elastin gene expression, or suppressing or reducing matrix metalloproteinase production.

15. A cosmetic, comprising the extract mixture as claimed in claim 1, wherein the cosmetic is in a dosage form comprising a solution, a suspension, a spray, a liquid lotion, a mousse, a gel, a lotion, a microemulsion, a cream, an ointment, a stick, a soap bar, a powder or a patch.

16. The cosmetic as claimed in claim 15, comprising a facial cleanser, a makeup remover, a soap, a body wash, a shampoo, a toner, a face cream, a primer, a serum, a sunscreen, a tinted moisturizer, a liquid foundation, a foundation compact, a hand cream, a body lotion or a facial mask.

* * * * *